United States Patent
Philippe et al.

(10) Patent No.: US 6,207,173 B1
(45) Date of Patent: Mar. 27, 2001

(54) LYSINE DERIVATIVES CONTAINING AN $N^\epsilon$-ALKOXY OR $N^\epsilon$-ALKENOXYCARBONYL GROUP, THEIR PREPARATION AND THEIR USE IN COSMETIC, PHARMACEUTICAL, HYGIENE OR FOOD COMPOSITIONS

(75) Inventors: Michel Philippe, Wissous; Thierry Bordier, Livry Gargan, both of (FR)

(73) Assignee: L'Oreal, Paris (FR)

( * ) Notice: Subject to any disclaimer, the term of this patent is extended or adjusted under 35 U.S.C. 154(b) by 0 days.

(21) Appl. No.: 09/298,180

(22) Filed: Apr. 23, 1999

Related U.S. Application Data

(63) Continuation of application No. 08/905,082, filed on Aug. 1, 1997, now abandoned, which is a continuation of application No. 08/334,313, filed on Nov. 2, 1994, now Pat. No. 5,684,178.

(30) Foreign Application Priority Data

Nov. 5, 1993 (FR) .................................................. 93 13188

(51) Int. Cl.$^7$ ................................ A61K 9/00; A61K 7/00
(52) U.S. Cl. ........................... 424/400; 424/401; 424/59; 424/60; 424/64; 514/551; 514/844; 560/159; 554/107; 554/110
(58) Field of Search ................................... 424/400, 401, 424/59, 60, 64; 514/551, 844; 560/159; 554/107, 110

(56) References Cited

U.S. PATENT DOCUMENTS

| 3,541,135 | 11/1970 | Johl et al. ................ 560/41 |
| 4,948,594 | 8/1990 | Abdel-Monem et al. ......... 426/2 |
| 5,206,012 | 4/1993 | Farer et al. ................ 424/69 |

FOREIGN PATENT DOCUMENTS

| 0139481 | 5/1985 | (EP) . |
| 0336265 | 10/1989 | (EP) . |
| 0447287 | 9/1991 | (EP) . |

OTHER PUBLICATIONS

H. Gueniffey et al., "Greffage D'Acides Amines Possedant Une Troisieme Fonction Sur Un Polymere, 2", *Makromolekulare Chemie, Macromolecular Chemistry and Physics*, vol. 177, Nov. 1976 pp. 3113–3118.

D. Wheeler, "Lipstick, Powder & Patents", *Soap, Perfumery & Cosmetics*, vol. 65, No. 1, Jan. 1992, pp. 25–26.

Primary Examiner—Rosalynd Keys
(74) Attorney, Agent, or Firm—Oliff & Berridge, PLC

(57) ABSTRACT

Lysine derivatives, salts of the derivatives, their optical isomers of D or L configuration, or their mixtures, the derivatives containing an $N^e$-alkoxy or $N^e$-alkenoxycarbonyl group and having the formula:

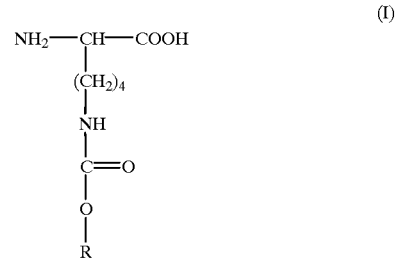

in which:

R represents a linear or branched $C_{13}$–$C_{24}$ alkyl radical or alkenyl radicals, are used in cosmetic, pharmaceutical, hygiene or food compositions, particularly compact compositions.

13 Claims, No Drawings

LYSINE DERIVATIVES CONTAINING AN $N^\epsilon$-ALKOXY OR $N^\epsilon$-ALKENOXYCARBONYL GROUP, THEIR PREPARATION AND THEIR USE IN COSMETIC, PHARMACEUTICAL, HYGIENE OR FOOD COMPOSITIONS This is a Continuation of application Ser. No. 08/905,082 filed Aug. 1, 1997, now abandoned, which in turn is a continuation of application Ser. No. 08/334,313, filed Nov. 2, 1994, now U.S. Pat. No. 5,684,178. The entire disclosure of the prior application(s) is hereby incorporated by reference herein in its entirety.

FIELD OF THE INVENTION

The subject of the present invention is new lysine derivatives containing an $N^\epsilon$-alkoxy or $N^\epsilon$-alkenoxycarbonyl group, their preparation and their use, especially as agents which make it possible to facilitate compaction in cosmetic, pharmaceutical, hygiene or food compositions.

BACKGROUND

There have been described, in EP-139,481, cosmetic compositions using, as agents for modifying the surface of inorganic compounds, for the purpose of increasing the dispersibility thereof, either an N-monoacylated derivative of a basic amino acid in which the aliphatic acyl group has from 8 to 22 carbon atoms or an N,N-diacylated derivative of a basic amino acid in which the aliphatic acyl groups, which are identical or different, having from 1 to 22 carbon atoms.

There have also been described, in EP-336,265, cosmetic compositions for hair shaping comprising, as surface-active agents, an N-monoacylated derivative of a basic amino acid in which the aliphatic acyl group has from 8 to 22 carbon atoms.

The acylated derivatives of the basic amino acids described previously are, however, very difficult and even impossible to compact.

Now, it is known that certain cosmetic, pharmaceutical and hygiene compositions are presented in the so-called "compact" form. They are anhydrous compositions consisting mainly of solid particles and of a fatty binder (oils or mixture of oils and waxes) and are shaped by compression or by pouring into a container which acts as mold.

The development of such compositions raises, however, many difficulties because the final product must be sufficiently homogeneous and compact to have a good ability to be removed and, moreover, to avoid fragmentation which may be caused, especially, by impacts.

SUMMARY OF THE INVENTION

According to the present invention, there is provided a family of compounds comprising lysine derivatives, the salts of the derivatives, as well as their optical isomers of D or L configuration, or their mixtures, the derivatives containing an $N^\epsilon$-alkoxy or $N^\epsilon$-alkenoxycarbonyl group and having a formula:

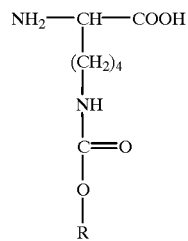

in which:

R represents a linear or branched $C_8$–$C_{24}$ alkyl radical or a linear or branched $C_8$–$C_{24}$ alkenyl radical.

The present invention also relates to a process for preparing these lysine derivatives and their use in cosmetic, pharmaceutical, hygiene or food compositions.

DESCRIPTION OF PREFERRED EMBODIMENTS

It has now been surprisingly and unexpectedly observed that a new family of lysine derivatives containing an $N^\epsilon$-alkoxy or $N^\epsilon$-alkenoxycarbonyl group made it possible not only to satisfy the abovementioned requirements and to facilitate the preparation of such compositions, in contrast to the corresponding $N^\epsilon$-acylated derivatives, but also to confer particularly advantageous spreading, skin-adhesion and light-scattering qualities, as well as a pleasant and smooth feel, from any cosmetic composition containing them.

The subject of the present invention is therefore lysine derivatives containing an $N^\epsilon$-alkoxy or $N^\epsilon$-alkenoxycarbonyl group of formula:

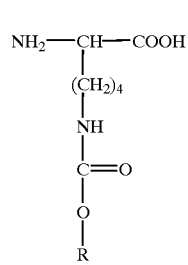

in which:

R represents a linear or branched $C_{13}$–$C_{24}$ alkyl radical, the $C_{16}$ radical being branched, or a linear or branched $C_8$–$C_{24}$ alkenyl radical, and the salts of the compounds of formula (I) as well as their optical isomers of D or L configuration or their mixtures.

Mention may be made, among the salts of the compounds of formula (I), of the salts of monovalent inorganic cations such as those of sodium, or of the salts of divalent inorganic cations such as those of zinc or of copper and of the salts of organic cations such as those of aminopropanediol, of trishydroxyaminomethane, of glucamine and of N-methylglucamine.

Mention may be made, among the compounds of formula (I), of, in particular, $N^\epsilon$-2-hexyldecyloxycarbonyl-L-lysine, $N^\epsilon$-2-decyltetradecyloxycarbonyl-L-lysine and $N^\epsilon$-tetradecyloxycarbonyl-L-lysine.

The compounds according to the invention are provided in the solid form having a particle size of between 10 nm and 500 μm and preferably between 0.1 and 25 μm.

They have little solubility both in oils and in aqueous solutions whose pH is between 5 and 8.

They have a high melting point, that is to say greater than 250° C., a high ability to reflect light and excellent adherence to the skin.

Another subject of the invention is a process for the preparation of the compounds of formula (I).

This process consists in reacting lysine or one of its salts, of known configuration, in aqueous medium and at basic pH, with a solution of a copper salt, in and then reacting the solution of the copper complex thus obtained of formula:

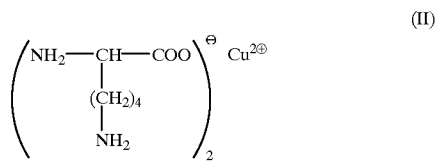

(II)

with a compound of formula:

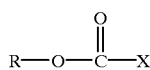

(III)

in which:

R is as defined previously, and X is chosen from the group consisting of a chlorine atom, a chloromethyl radical or an imidazolyl radical, the compound of formula (III) being added without solvent, and treating the copper salt of the $N^\epsilon$-substituted lysine obtained with a decomplexing agent and, optionally, purifying the compound obtained.

Mention may in particular be made, among the copper salt solutions used in the process according to the invention, of copper sulphate solutions.

The basic pH of the reaction medium is preferably between 8 and 14.

According to a preferred embodiment of the process for the preparation of the compounds of formula (I) according to the invention, the decomplexing agent used is an aqueous solution of the disodium salt of ethylenediaminetetraacetic acid.

Another subject of the present invention is cosmetic, pharmaceutical, hygiene or food compositions comprising a lysine derivative corresponding to the following formula:

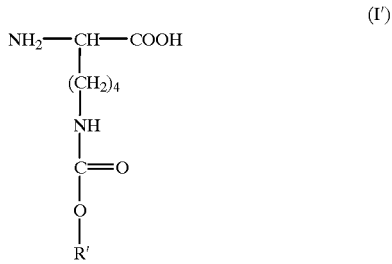

(I')

in which:

R' represents a linear or branched $C_8$–$C_{24}$ alkyl or alkenyl radical, and the salts of the compounds of formula (I')as well as their optical isomers of D or L configuration or their mixtures.

Mention may especially be made, among the compounds of formula (I'), of $N^\epsilon$-2-ethylhexyloxycarbonyl-L-lysine, $N^\epsilon$-dodecyloxycarbonyl-L-lysine, $N^\epsilon$-hexadecyloxycarbonyl-L-lysine, $N^\epsilon$-decyloxycarbonyl-L-lysine, $N^\epsilon$-2-butyloctyloxycarbonyl-L-lysine, $N^\epsilon$-2-hexyldecyloxycarbonyl-L-lysine, $N^\epsilon$-2-decyltetradecyloxycarbonyl-L-lysine and $N^\epsilon$-tetradecyloxycarbonyl-L-lysine.

Some of the compounds of formula (I') are known and have been described in U.S. Pat. No. 3,541,135 as intermediates of active compounds in the treatment of allergies and inflammations.

The proportion of lysine derivative of formula (I') in the compositions according to the invention is preferably between 0.05% and 80% by weight with respect to the total weight of the composition and in particular between 1% and 30% by weight.

Of course, the lysine derivatives according to the invention can be present in the compositions according to the invention in the free form or in the form of a combination with the substrate particles which they coat as mentioned hereinbelow.

The compositions according to the invention can be provided in various forms such as dispersions, optionally thickened or gelled lotions, optionally "compacted" powders, milks, creams, sticks or alternatively foams or sprays when they are packaged as aerosols.

They can especially be oil-in-water or water-in-oil emulsions, vesicular dispersions or alternatively solid preparations.

The compositions according to the invention can especially be provided in the form of cosmetic make-up compositions such as foundation creams, tinted creams, mascaras, blushers, eye shadows, lipsticks, nail varnishes and exfoliative compositions.

According to a specific embodiment of the compositions according to the invention, the latter are provided in the so-called "compact" form, the compounds of general formula (I') facilitating compaction of the ingredients of the said compositions.

Mention may especially be made, among these so-called compact compositions, of foundation creams, blushers, eye shadows and lipsticks.

The compositions can also be pharmaceutical or hygiene compositions such as toothpastes, powders for the body or for babies and anti-perspirant powders.

In addition to the compounds of formula (I'), the compositions according to the invention can comprise at least one additive chosen from the group consisting of surface-active agents, fatty substances, organic solvents, silicones, thickeners, emollients, sunscreening agents, treating agents, anti-foaming agents, moisturizing agents, fragrances, preservatives, anti-oxidizing agents, sequestrants, flavouring agents, basifying or acidifying agents, fillers and inorganic or organic powders.

Mention may be made, among the surface-active agents which can be used in the compositions according to the invention which are provided in the emulsion form, of conventional surface-active agents whether they are anionic, cationic, non-ionic or amphoteric in nature or of a mixture of the said surface-active agents.

Mention may be made, among the fatty substances which can be used in the compositions according to the invention, of oils, waxes, fatty acids, fatty alcohols or a mixture of the said fatty substances.

The oils can be of animal, plant, inorganic or synthetic origin. Mention may in particular be made of hydrogenated palm oil, hydrogenated castor oil, liquid paraffin and purcellin oil.

The waxes can be of animal, plant, inorganic or synthetic origin. Mention may in particular be made of beeswax, montan wax, carnauba wax, candelilla wax, sugar cane wax, Japan wax, ozocerite, microcrystalline waxes, paraffin wax, lanolin wax, hydrogenated lanolin wax and acetylated lanolin wax.

Mention may especially be made, among the fillers which can be used in the compositions according to the invention, of optionally coloured insoluble fillers such as pigments, for example metal oxides such as titanium, zinc, iron, manganese, cerium and/or zirconium oxides, and their nanopigments, or nylon, polyethylene, mica or talc powders.

Another subject of the present invention is the use of the lysine derivatives of formula (I') as substances for coating substrate particles which make it possible to confer better properties on the said particles and in particular to increase the compressibility thereof and to improve the feel of the cosmetic compositions containing them.

Mention may especially be made, among the particles which can thus be coated, of pigments and of particulate fillers such as mentioned hereinabove and of microspheres such as the hollow vinylidene chloride/acrylonitrile copolymer microspheres marketed under the names of "Expancel 551 DE 20" and "Expancel 551 DE" by the Company Casco Nobel.

Examples of the preparation of the lysine derivatives containing an $N^\epsilon$-alkoxy or $N^\epsilon$-alkenoxycarbonyl group, and of various compositions containing them, will now be given by way of illustration.

PREPARATION EXAMPLES

Example 1

Preparation of $N^\epsilon$-dodecyloxycarbonyl-L-lysine 15 g (82.1 mmol) of L-lysine monohydrochloride are dissolved, at room temperature, in 66 ml of a 10% aqueous sodium hydroxide solution in a 250 ml three-necked flask equipped with a thermometer and a 50 ml dropping funnel.

10.2 g (41.06 mmol) of copper sulphate pentahydrate, dissolved beforehand in 30 ml of water, are then added. After homogenization, the reaction medium is cooled to a temperature of 5° C.

8.2 g (82.1 mmol) of sodium hydrogencarbonate are then added and then 19.3 g (82.1 mmol) of dodecyl chloroformate are added dropwise. After leaving overnight at room temperature, the reaction medium is filtered and the blue precipitate thus obtained is washed with water and then dried over phosphorus pentoxide. The crude product, in the blue copper complex form, is then treated with a 10% aqueous solution of the dihydrated disodium salt of ethylenediaminetetraacetic acid (120 mmol) at reflux for four hours and the mixture is then cooled, the precipitate filtered off, washed with water and with acetone and then dried.

This treatment is then repeated until a white product is obtained.

There are thus obtained, with a yield of 74%, 21.8 g of $N^\epsilon$-dodecyloxycarbonyl-L-lysine, existing in the form of a white powder.

Analyses:

Melting point: >260° C. (Kofler)

Mass spectrum: (TSQ 70 CI-DCI): m/Z: 359(M+H), 315 (M—$CO_2$+H)$^+$, 169($C_{12}H_{25}^+$)

The NMR spectra are recorded on a Bruker WM 250

$^1$H NMR ($CD_3COOD$):

4.12 ppm (3H, m, $CH_2$-12 and CH-18);

3.22 ppm (2H, t, $CH_2$-14);

1.26 to 1.67 ppm (26H, m, $CH_2$-2 to 11 and 15 to 17);

0.95 ppm (3H, t, $CH_3$-1)

Elemental analysis $C_{19}H_{38}N_2O_4$; MW=358.526

|  | C % | H % | N % | O % |
|---|---|---|---|---|
| Calculated | 63.65 | 10.68 | 7.81 | 17.85 |
| Found | 63.43 | 10.65 | 8.05 | 17.88 |

Presence of copper: 695 ppm

Particle size measured using a Coulter counter TA II: Mean size (in number)=2.23 μm Standard deviation=1.36 μm.

Example 2

Preparation of $N^\epsilon$-hexadecyloxycarbonyl-L-lysine

According to the same procedure as described in Example 1, 29.1 g of $N^\epsilon$-hexadecyloxycarbonyl-L-lysine (Yield 85.5%), existing in the form of a white powder, are obtained by using 25 g (82.1 mmol) of hexadecyl chloroformate.

Analyses:

Melting point: >260° C. (Kofler)

Mass spectrum: (TSQ 70 CI-DCI): m/Z: 415(MH), 367.2, 279.1, 225.1

Elemental analysis $C_{23}H_{46}N_2O_4$; MW=414.634

|  | C % | H % | N % | O % |
|---|---|---|---|---|
| Calculated | 66.56 | 11.09 | 6.75 | 15.43 |
| Found | 66.70 | 11.07 | 6.58 | 15.18 |

Presence of copper: 0.45%

Particle size measured using a Coulter counter TA II: Mean size (in number)=4.58 μm Standard deviation=5.62 μm.

Example 3

Preparation of $N^\epsilon$-2-ethylhexyloxycarbonyl-L-lysine

According to the same procedure as described in Example 1, 8.4 g of $N^\epsilon$-2-ethylhexyloxycarbonyl-L-lysine (Yield 34%), existing in the form of a white powder, are obtained by using 14.8 g (82.1 mmol) of 2-ethylhexyl chloroformate.

Analyses:

Melting point: >260° C. (Kofler)

The NMR spectra are recorded on a Bruker WM 250

$^1$H NMR ($CD_3COOD$)

4.07 to 4.15 ppm (3H, t+m, $CH_2$-8 and CH-14;

3.23 ppm (2H, t, $CH_2$-10);

1.98 to 2.1 ppm (2H, m, $CH_2$-13);
1.38 to 1.61 ppm (13H, m, $CH_2$-2 to 4 and 6, 11, 12 and CH-5);
0.97 ppm (6H, 2t, $CH_3$-1 and 7)
Elemental analysis $C_{15}H_{30}N_2O_4$; MW=302.417

|  | C % | H % | N % | O % |
|---|---|---|---|---|
| Calculated | 59.58 | 10.00 | 9.26 | 21.16 |
| Found | 58.83 | 10.06 | 9.13 | 21.65 |

Presence of copper: 100 ppm
Particle size measured using a Coulter counter TA II: Mean size (in number): 2.57 μm
Standard deviation=1.86 μm.

Example 4

$N^\epsilon$-Decyloxycarbonyl-L-lysine

According to the same procedure as described in Example 1, $N^\epsilon$-decyloxycarbonyl-L-lysine, existing in the form of a white powder, is obtained by using decyl chloroformate as alkyl chloroformate.
Analyses:
Melting point: 244.9° C. (DSC Mettler)
Mass spectrum: (SSQ 710 CI-DI): m/Z: 331 $(MR)^+$
The NMR spectra are recorded on a Bruker AMXS
$^1H$ NMR ($CD_3COOD$):
4.17 ppm (2H, t, $CH_2$-10);
4.10 ppm (1H, m, CH-16);
3.25 ppm (2H, t, $CH_2$-12);
2.06 ppm (2H, m, $CH_2$-15);
1.70 ppm (2H, m, $CH_2$-9);
1.64 ppm (2H, m, $CH_2$-13);
1.40 ppm (16H, m, $CH_2$-2 to 8 and 14);
0.970 ppm (3H, t, $CH_3$-1).
Elemental analysis $C_{17}H_{34}N_2O_4$; MW=330.5

|  | C % | H % | N % | O % |
|---|---|---|---|---|
| Calculated | 61.72 | 10.29 | 8.47 | 19.36 |
| Found | 61.91 | 10.50 | 8.41 | 19.43 |

Presence of copper: 340 ppm
Particle size measured by light scattering using a Leeds & Worthrup model Microtrac X100 at 0.4% in a water/ethanol (1/1) mixture: Mean size (in number): 0.69 μm.

Example 5

$N^\epsilon$-2-Butyloctyloxycarbonyl-L-lysine

According to the same procedure as described in Example 1, $N^\epsilon$-2-butyloctyloxycarbonyl-L-lysine, existing in the form of a white powder, is obtained by using 2-butyloctyl chloroformate as alkyl chloroformate.
Analyses:
Melting point: ≧260° C. (Baukofler)
Mass spectrum: (SSQ 710 CI-DI): m/Z: 359 $(MH)^+$
The NMR spectra are recorded on a Bruker AMX 500
$^1H$ NMR ($d_6$-DMSO +$CD_3COOD$):
3.81 ppm (2H, d, $CH_2$-12);
3.52 ppm (1H, dd, CH-18);
2.94 ppm (2H, t, $CH_2$-14);
1.66 to 1.77 ppm (2H, 2m, $CH_2$-17);
1.51 ppm (1H, m, CH-7);
1.21 to 1.40 (20H, m, $CH_2$-2 to 6, 8 to 10 and 15, 16);
0.82 ppm (6H, 2t, $CH_3$-1 and 11).
Elemental analysis $C_{19}H_{38}N_2O_4$; MW=358.526

|  | C % | H % | N % | O % |
|---|---|---|---|---|
| Calculated | 63.65 | 10.68 | 7.81 | 17.85 |
| Found | 63.78 | 10.69 | 7.75 | 18.14 |

Presence of copper: 60 ppm
Particle size measured by light scattering using a Leeds & Worthrup model Microtrac X100 at 0.4% in a water/ethanol (1/1) mixture: Mean size (in number): 1.66 μm.

Example 6

Zinc $N^\epsilon$-dodecyloxcyarbonyl-L-lysinate 5 g (13.9 mmol) of $N^\epsilon$-dodecyloxycarbonyl-L-lysine obtained in Example 1 are dissolved at 70° C. in 5.6 ml of a 10% aqueous sodium hydroxide solution and 50 ml of water in a 250 ml beaker.

2 g of zinc sulphate heptahydrate, dissolved beforehand in 10 ml of water, are then added dropwise.

The reaction mixture is filtered and the white precipitate thus obtained is washed with water and then dried.

There are thus obtained, with a yield of 96%, 5.2 g of zinc $N^\epsilon$-dodecyloxycarbonyl-L-lysinate, existing in the form of a white powder.
Analyses:
Melting point: >260° C. (Baukofler)
Elemental analysis: $2C_{19}H_{37}N_2O_4$—Zn; MW=780.405

|  | C % | H % | N % | O % | Zn % |
|---|---|---|---|---|---|
| Calculated | 58.49 | 9.56 | 7.18 | 16.4 | 8.38 |
| % Calc. (+1.2 mol $H_2O$) | 56.85 | 9.52 | 6.98 | 18.35 | 8.15 |
| Found | 56.88 | 9.25 | 7.09 | 18.91 | 8.00 |

Particle size measured by light scattering using a Leeds & Worthrup model Microtrac X 100 at 0.4% in a water/ethanol (1/1) mixture: Mean size (in number): 0.85 μm.

COMPOSITION EXAMPLES

Example I

Compact powder

Phases A and B are prepared separately by mixing the following ingredients:

| Phase A: | |
|---|---|
| Talc | 36.7 g |
| Bismuth oxychloride | 10 g |
| Zinc stearate | 4 g |
| $N^\epsilon$-dodecyloxycarbonyl-L-lysine | 20 g |
| Nylon 12 powder marketed under the name of "Orgasol 2082 D Nat Extra Cos" by the Company Atochem | 20 g |
| Fragrance | 1.6 g |

-continued

| | |
|---|---|
| Hollow microspheres marketed under the name of "Expancel 551 DE 20" by the Company Casco Nobel | 0.1 g |
| Yellow iron oxide marketed under the name of "Sicomet Yellow 10" by the Company BASF | 0.6 g |
| Mixture of brown iron oxide and of yellow iron oxide marketed under the name of "Sicomet Brown ZP 3569" by the Company BASF | 0.8 g |
| Black iron oxide marketed under the name of "Sicomet Black 85" by the Company BASF | 0.2 g |
| Phase B: | |
| Liquid paraffin | 6 g |

All the ingredients of Phase A are gently ground for 5 minutes and then Phase B is added. The mixture is then ground gently for 2 minutes and then vigorously for 3 minutes.

The composition is then sieved using a 0.160 mm sieve and the preparation is divided up into small dishes and then compacted at a pressure of 60 bar.

The compacted powder thus obtained has a satisfactory hardness which is highly resistant to impacts.

The compacted powder disintegrates easily and is readily spread on the skin, showing a highly satisfactory adherence.

Example II

Lipsticks

The following ingredients are mixed:

| | |
|---|---|
| Jojoba oil | 11.65 g |
| Sesame oil | 11.31 g |
| Di-tert-butyl-4-hydroxytoluene marketed under the name of "Antracine 8" by the Company Jan Dekker | 0.07 g |
| Stabilized isopropyl lanolate marketed under the name of "Lanesta SLPV" by the Company Westbrook | 12.48 g |
| 2-Ethylhexyl glyceryl behenate marketed under the name of "Mexanyl GQ" by the Company Chimex | 11.31 g |
| Polybutylene marketed under the name of "Indopol H 300" by the Company Amoco Chemical | 12.48 g |

The mixture is heated on a water bath for one hour at a temperature between 60 and 70° C. and the mixture of the following ingredients is then added:

| | |
|---|---|
| Calcium lake of Lithol Red B on colophony marketed under the name of "DC Red 7 WOO5" by the Company Wackherr | 2.1 g |
| Aluminium lake of Brilliant Yellow FCF on alumina marketed under the name of "FDC Yellow 6 A1 Lake BC - 6508" by the Company Clark Color | 7.32 g |
| Yellow iron oxide | 0.2 g |
| Mixture of brown iron oxide and of yellow iron oxide marketed under the name of "Sicomet Brown ZP 3569" by the Company BASF | 1.35 g |
| Unprocessed rutile titanium oxide marketed under the name of "Hombitan R 301" by the Company Sachtleben | 0.649 g |

The mixture thus obtained is ground using a Discontimill grinder and then the mixture of the following ingredients is added:

| | |
|---|---|
| Beeswax | 3.18 g |
| Polyethylene wax marketed under the name of "Polywax 500" by the Company Bareco | 12.74 g |
| Oxypropylenated lanolin wax marketed under the name of "Propoxyol 1695" by the Company Henkel | 12.86 g |

After heating the mixture for one hour at 100° C., a homogeneous mixture is obtained to which 0.3 g of fragrance is added. When the temperature of the mixture has come down again to approximately 60° C., 2 g of $N^\epsilon$-dodecyloxycarbonyl-L-lysine are added and the mixture is then poured into molds.

The lipsticks thus obtained are simultaneously homogeneous, compact and have good resistance to impacts.

They are readily applied to the lips, are smooth and have good hold.

Example III

Make-up removal cream

The following ingredients are mixed:

| | |
|---|---|
| Sorbitan monostearate marketed under the name of "Span 60" by the Company ICI Surfactants | 6 g |
| Polyglycerolated oleyl alcohol marketed under the name of "Chimexane NB" by the Company Chimex | 4 g |
| Allantoin | 0.2 g |
| D-Panthenol | 0.8 g |
| Water | 78.98 g |

After heating the mixture at 80° C., 10 g of $N^\epsilon$-dodecyloxycarbonyl-L-lysine are added with stirring using a Moritz stirrer and the mixture is then homogenized.

When the temperature of the mixture has come down again to approximately 40° C., 0.02 g of preservative, marketed under the name of "Kathon CG" by the Company Rohm-Haas, is added.

The cream thus obtained is readily applied to the skin and is very smooth.

Example IV

Lipsticks

Lipsticks are prepared, according to the same procedure as described in Example II, from the following ingredients:

| | |
|---|---|
| Jojoba oil | 11.65 g |
| Sesame oil | 11.31 g |
| Di-tert-butyl-4 -hydroxytoluene marketed under the name of "Antracine 8" by the Company Jan Dekker | 0.07 g |
| Stabilized isopropyl lanoolate marketed under the name of "Lanesta SLPV" by the Company Westbrook | 12.48 g |
| 2-Ethylhexyl glyceryl behenate marketed under the name of "Mexanyl GQ" by the | 11.31 g |

-continued

| | |
|---|---|
| Company Chilex | |
| Polybutylene marketed under the name of "Indopol H 300" by the Company Amoco Chemical | 12.48 g |
| Calcium lake of Lithol Red B on colophony marketed under the name of "DC Red 7 WOO5" by the Company Wackherr | 2.1 g |
| Alumnium lake of Brilliant Yellow FCF on alumina marketed under the name of "FDC Yellow 6 A1 Lake BC - 6508" by the Company Clark Color | 7.32 g |
| Yellow iron oxide | 0.2 g |
| Mixture of brown iron oxide and of yellow iron oxide marketed under the name of "Sicomet Brown ZP 3569" by the Company BASF | 1.35 g |
| Unprocessed rutile titanium oxide marketed under the name of "Hombitan R 301" by the Company Sachtleben | 0.649 g |
| Beeswax | 3.18 g |
| Polyethylene wax marketed under the name of "Polywax 500" by the Company Bareco | 12.74 g |
| Oxypropylenated lanolin wax marketed under the name of "Propoxyol 1695" by the Company Henkel | 12.86 g |
| $N^\epsilon$-2-Butyloctyloxycarbonyl-L-lysine | 2.0 g |

The lipsticks thus obtained are simultaneously homogeneous, compact and have good resistance to impacts.

They are readily applied to the lips, are smooth and have good hold.

Example V

Lipsticks

Lipsticks are prepared, according to the same procedure as described in Example II, from the following ingredients:

| | |
|---|---|
| Jojoba oil | 11.65 g |
| Sesame oil | 11.31 g |
| Di-tert-butyl-4 hydroxytoluene marketed under the name of "Antracine 8" by the Company Jan Dekker | 0.07 g |
| Stabilized isopropyl lanolate marketed under the name of "Lanesta SLPV" by the Company Westbrook | 12.48 g |
| 2-Ethylhexyl glyceryl behenate marketed under the name of "Mexanyl GQ" by the Company Chimex | 11.31 g |
| Polybutylene marketed under the name of "Indopol H 300" by the Company Amoco Chemical | 12.48 g |
| Calcium lake of Lithol Red B on colophony marketed under the name of "DC Red 7 WOO5" by the Company Wackherr | 2.1 g |
| Aluminium lake of Brilliant Yellow FCF on alumina marketed under the name of "FDC Yellow 6 A1 Lake BC - 6508" by the Company Clark Color | 7.32 g |
| Yellow iron oxide | 0.2 g |
| Mixture of brown iron oxide and of yellow iron oxide marketed under the name of "Sicomet Brown ZP 3569" by the Company BASF | 1.35 g |
| Unprocessed rutile titanium oxide marketed under the name of "Hombitan R 301" by the Company Sachtleben | 0.649 g |
| Beeswax | 3.18 g |
| Polyethylene wax marketed under the name of "Polywax 500" by the Company Bareco | 12.74 g |
| Oxypropylenated lanolin wax marketed under the name of "Propoxyol 1695" by the Company Henkel | 12.86 g |
| Zinc $N^\epsilon$-dodecyloxycarbonyl-L-lysinate | 2.0 g |

The lipsticks thus obtained are simultaneously homogeneous, compact and have good resistance to impacts.

They are readily applied to the lips, are smooth and have good hold.

What is claimed is:

1. A composition comprising from 0.05 to 80% by weight with respect to the total weight of the composition of at least one compound selected from the group consisting of a lysine derivative having the formula:

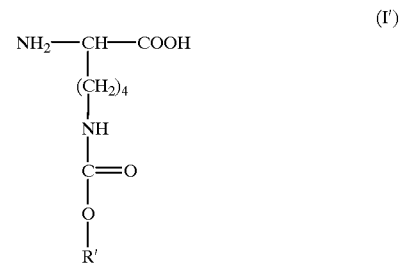

(I')

in which R' represents a linear or branched $C_{13}$–$C_{24}$ alkyl or $C_{13}$–$C_{24}$ alkenyl radical, the salts of said derivative, the optical isomers of D or L configuration and mixtures thereof, and wherein said composition is a cosmetic, pharmaceutical, hygienic or food composition.

2. The composition according to claim 1, wherein the at least one lysine derivative of formula (I') is selected from the group consisting of $N^\epsilon$-2-hexadecyloxy-$N^\epsilon$-2-hexyldecyloxycarbonyl-L-lysine, $N^\epsilon$-2-decyltetradecyloxycarbonyl-L-lysine and $N^\epsilon$-tetradecyloxycarbonyl-L-lysine.

3. The composition according to claim 1, wherein said at least one lysine derivative is present in a proportion of between 1% and 30% by weight with respect to the total weight of the composition.

4. The composition according to claim 1, wherein said composition additionally contains at least one additive selected from the group consisting of surface-active agents, fatty substances, organic solvents, silicones, thickeners, emollients, sunscreening agents, anti-foaming agents, moisturizing agents, fragrances, preservatives, antioxidizing agents, sequestrants, flavoring agents, basifying or acidifying agents, fillers and inorganic or organic powders.

5. The composition according to claim 1, wherein the composition is a compact composition.

6. The composition of claim 5, wherein the composition is a compact cosmetic composition.

7. The composition of claim 5, wherein the composition further comprises a fatty binder.

8. The composition of claim 5, wherein the composition is anhydrous.

9. A composition according to claim 1, wherein R' represents a linear or branched $C_{13}$–$C_{24}$ alkenyl radical.

10. A compact cosmetic composition comprising from 0.05 to 80% by weight with respect to the total weight of the composition of at least one compound to facilitate the compaction of the ingredients of said composition, said compound being selected from the group consisting of a lysine derivative having the formula:

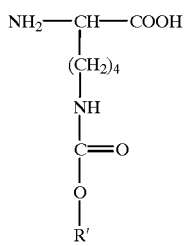

(I')

in which R' represents a linear or branched $C_{13}$–$C_{24}$ alkyl or $C_{12}$–$C_{24}$ alkenyl radical, the salts of said derivative, the optical isomers of D or L configuration and mixtures thereof.

11. The compact cosmetic composition according to claim 10, wherein R' represents a linear or branched $C_{13}$–$C_{24}$ alkenyl radical.

12. A compact pharmaceutical composition comprising from 0.05 to 80% by weight with respect to the total weight of the composition of at least one compound to facilitate the compaction of the ingredients of said composition, said compound being selected from the group consisting of a lysine derivative having the formula:

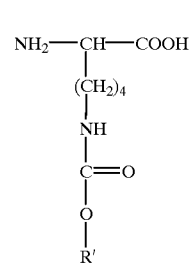

(I')

in which R' represents a linear or branched $C_{13}$–$C_{24}$ alkyl or $C_{13}$–$C_{24}$ alkenyl radical, the salts of said derivative, the optical isomers of D or L configuration and mixtures thereof.

13. The compact pharmaceutical composition according to claim 12, wherein R' represents a linear or branched $C_{13}$–$C_{24}$ alkenyl radical.

* * * * *